(12) United States Patent
Kamiyama et al.

(10) Patent No.: US 8,379,196 B2
(45) Date of Patent: Feb. 19, 2013

(54) METHOD FOR JUDGING WHETHER SEMICONDUCTOR WAFER IS NON-DEFECTIVE WAFER BY USING LASER SCATTERING METHOD

(75) Inventors: Eiji Kamiyama, Tokyo (JP); Takashi Nakayama, Tokyo (JP); Takeo Katoh, Tokyo (JP)

(73) Assignee: Sumco Corporation, Tokyo (JP)

( * ) Notice: Subject to any disclaimer, the term of this patent is extended or adjusted under 35 U.S.C. 154(b) by 394 days.

(21) Appl. No.: 12/792,148

(22) Filed: Jun. 2, 2010

(65) Prior Publication Data

US 2010/0309461 A1    Dec. 9, 2010

(30) Foreign Application Priority Data

Jun. 8, 2009   (JP) ................................ 2009-137105

(51) Int. Cl.
    *G01N 21/00*   (2006.01)
(52) U.S. Cl. .................... 356/237.2; 356/237.1
(58) Field of Classification Search ..... 356/237.1–237.6
    See application file for complete search history.

(56) References Cited

U.S. PATENT DOCUMENTS

2006/0192949 A1   8/2006   Bills et al.
2008/0018887 A1   1/2008   Chen et al.

FOREIGN PATENT DOCUMENTS

JP   63-140904    6/1988
WO   2007/137261  11/2007

OTHER PUBLICATIONS

Eiji Kamiyama, "Surface Inspection of Silicon-on-Insulator Wafers with Ultra Thin Top-Si Layer by Laser Scattering," Jpn. J. Appl. Phys., vol. 45, No. 2A (2006), pp. 630-637, Feb. 8, 2006.
K. Umezawa et al, "Advanced Surface Cleanness Evaluation Technique Using Epitaxial Silicon Germanium (SiGe) Process beyond 32nm Node," "ISSM Paper: YE-O-184," In: "Conference Proceedings of the IEEE 2007 International Symposium on Semiconductor Manufacturing," 2007, Institute of Electrical and Electronic Engineers , USA , XP002590739, ISBN: 978-1-4244-1142-9 , pp. 572-575, 2007.

*Primary Examiner* — Tri T Ton
(74) *Attorney, Agent, or Firm* — Greenblum & Bernstein, P.L.C.

(57) ABSTRACT

A semiconductor wafer whose number of LPDs per wafer is equal to or smaller than a predetermined number is sorted out, and a judgment as to whether a semiconductor wafer is a non-defective wafer is made visually based on a haze map of the semiconductor wafer subjected to the sorting. Moreover, a semiconductor wafer whose number of LPDs per wafer is equal to or smaller than a predetermined number is sorted out. Then, from the semiconductor wafers subjected to the sorting, a semiconductor wafer whose in-plane standard deviation and in-plane average value of the haze signals in a wafer plane have a specific relationship is sorted out, and this semiconductor wafer is judged to be a non-defective wafer. In this way, a method for judging whether a semiconductor wafer is a non-defective wafer or a defective wafer, the method that can make a judgment more uniform and accurate without dependence on the difference in the S/N ratio between inspection apparatuses using a laser scattering method, is provided.

2 Claims, 5 Drawing Sheets

METHOD FOR JUDGING WHETHER SEMICONDUCTOR WAFER IS NON-DEFECTIVE WAFER BY USING LASER SCATTERING METHOD

BACKGROUND OF THE INVENTION

1. Field of the Invention

The present invention relates to a method for judging whether a semiconductor wafer is a non-defective wafer or not by inspecting the surface of a semiconductor wafer by a laser scattering method, the surface on which a device pattern has not yet been formed. More specifically, the present invention relates to a method for inspecting a semiconductor wafer by using a haze signal from an inspection apparatus using a laser scattering method.

2. Description of the Related Art

As a microelectronic device structure has recently become finer, dealing with particle induced defects and other defects on the surface of a semiconductor wafer on which a device pattern has not yet been formed has become extremely important. The particle induced defects and other defects near the surface of the semiconductor wafer greatly affect the quality of a semiconductor device. Therefore, to improve the quality of the device, it is necessary to evaluate the particle induced defects and other defects near the surface of the semiconductor wafer which becomes a substrate of the device and grasp the actual conditions of the particle induced defects and other defects.

Incidentally, semiconductor wafer manufacturers and device manufacturers conduct an inspection for evaluating these particle induced defects and other defects near the surface of the semiconductor wafer by using an apparatus (for example, refer to Patent Document 1) using scattered light generated when light is made to enter an object to be measured. Based on the number of LPDs (light point defects) on the wafer surface detected by an inspection apparatus using such a laser scattering method, a judgment is generally made as to whether the wafer is a non-defective wafer or a defective wafer. The inspection apparatus detecting the LPDs by the laser scattering method illuminates the wafer with a laser from above, condenses the scattered light from the LPDs with a condenser, converts the scattered light into an electrical signal with a photoelectric conversion element, and detects the electrical signal. However, since a requirement for an LPD detection lower limit is now below 65 nm and the intensity of scattering from the LPDs themselves is decreased, the judgment results obtained by the wafer manufacturer and the judgment results obtained by the device manufacturer do not necessarily coincide with each other. As a result, there are more and more cases in which the wafer judged to be a non-defective wafer by the wafer manufacturer is judged to be a defective wafer by the device manufacturer.

On the other hand, the scatter components from the wafer surface in such an inspection apparatus using a laser scattering method include a haze signal, which is a background signal from which a signal from the LPD is removed. The haze is the sum of the haze caused by microroughness in a wafer plane and the haze caused by light interference of a transparent film. As a result, as will be described later, the haze is different from the actual LPD. However, a requirement for an LPD detection lower limit is now below 65 nm, and a difference between the scattering intensity from the LPDs in the wafer plane and the scattering intensity from the haze is very small. Therefore, even in a wafer, which is judged to be non-defective in the inspection conducted by the wafer manufacturer, a spot in which the haze is partially high may be erroneously recognized as an LPD depending on the stability of the inspection apparatus of the device manufacturer.

It is for this reason that, even when the area recognized as including the LPD by the inspection apparatus is observed again with an SEM (scanning electron microscope), particle induced defects or other defects which become a problem in the device production process are often not found actually in that area. Such a disparity between the judgment results obtained by the wafer manufacturer and the judgment results obtained by the device manufacturer in the inspection of the LPDs conducted by using the laser scattering method often causes a problem such as a temporary suspension of the production line.

The inventors have found out that a sensory method of making a visual inspection of each haze map on which the haze signals are shown can prevent such a problem. However, such an inspection method by which a visual inspection of each haze map is made by the human eye results in delays in the production line. Therefore, as a cause of such a disparity between the judgment results obtained by the wafer manufacturer and the judgment results obtained by the device manufacturer based on the number of LPDs, the inventors have further focused attention on the stability of the inspection apparatus, in particular, the difference in the S/N ratio (signal/noise ratio) between the inspection apparatuses. That is, even when both the semiconductor wafer manufacturer and the device manufacturer judge whether a semiconductor wafer is a non-defective wafer or a defective wafer by the inspection apparatus using the laser scattering method, there may be a difference in judgment results when the inspection apparatuses have different numbers or are of different models. In addition, even when identical inspection apparatuses are used, there is a difference in judgment results due to the difference in the measurement mode or throughput settings or the difference in detectors provided in the identical inspection apparatuses. Here, S (signal) is scattered light, and N (noise) is incident light or the like.

In the inspection apparatus using the laser scattering method, the size of a particle induced defect or other defect as an LPD is determined based on the intensity of scattering from a PSL (polystyrene latex) standard particle. However, the apparatuses of different models have different laser illumination systems or scattered light detection systems, and therefore have different scattering behaviors in particle induced defects or other defects and different detection capabilities. As a result, a pattern on a haze map, the pattern recognized as haze in an apparatus, sometimes exceeds a threshold of the scattering intensity corresponding to an LPD size lower limit, and is erroneously detected as a pseudo LPD by another apparatus. The same erroneous detection can occur due to the difference in the measurement mode or detectors between the inspection apparatuses. Furthermore, the same erroneous detection can occur due to the difference in throughput settings. This is because, in a common inspection apparatus, the throughput is enhanced by making the beam spot diameter greater than a maximum sensitivity by sacrificing the sensitivity and reducing the number of scanning operations performed on the wafer. As a result, since even identical apparatuses use different reference calibration tables for the intensity of scattering from the PSL standard particle, the reference calibration tables provided one for each throughput, the same erroneous detection occurs due to a subtle difference in the scattering intensity in LPDs which are equal to or smaller than 65 nm, the LPDs in which the difference between S (signal) and N (noise) has become almost zero.

Such erroneous detection occurs not only between the inspection apparatuses using the laser scattering method, but also can occur even when, for example, the wafer manufacturer conducts an inspection with an inspection apparatus using the laser scattering method and the device manufacturer conducts an inspection with a bright-field inspection apparatus. This is because the bright-field apparatus uses light as in the inspection apparatus using the dark-field laser scattering method.

Patent Document 1

Japanese Examined Patent Application Publication No. 63-140904 (Claims)

Therefore, the inventors have focused attention on the haze map generated from the haze signals which are background signals in the LPD measurement performed with the inspection apparatus using the laser scattering method. As a result, for automation of an inspection using the haze signals, the inventors have found a method for judging whether a semiconductor wafer is a non-defective wafer or a defective wafer based on the relationship between the in-plane standard deviation and the in-plane average value of the haze signals, and solved the above problems.

SUMMARY OF THE INVENTION

The object of the present invention is to provide a method for judging whether a semiconductor wafer is a non-defective wafer or a defective wafer, the method that can make a judgment more uniform and accurate without dependence on the difference in the S/N ratio between inspection apparatuses using a laser scattering method.

According to a first aspect of the present invention, a method for judging whether a semiconductor wafer of a plurality of semiconductor wafers is a non-defective wafer based on the number of LPDs measured by setting a minimum size of an LPD to be detected at a predetermined value of 65 nm or less when the number of LPDs on the surfaces of the plurality of semiconductor wafers on which no device pattern is formed is measured for each wafer with a detecting apparatus using a laser scattering method, the method includes a step of: measuring the number of LPDs whose sizes are equal to or greater than the predetermined value in a wafer plane from the wafer surface on a wafer-by-wafer basis and generating a haze map for each wafer based on haze signals in the wafer plane; sorting out a semiconductor wafer whose number of measured LPDs per wafer is equal to or smaller than a predetermined number from the semiconductor wafers subjected to the measurement; and visually making a judgment as to whether a semiconductor wafer of the semiconductor wafers obtained by the sorting is a non-defective wafer based on the generated haze map.

According to a second aspect of the present invention, a method for judging whether a semiconductor wafer of a plurality of semiconductor wafers is a non-defective wafer based on the number of LPDs measured by setting a minimum size of an LPD to be detected at a predetermined value of 65 nm or less when the number of LPDs on the surfaces of the plurality of semiconductor wafers on which no device pattern is formed is measured for each wafer with a detecting apparatus using a laser scattering method, the method includes a step of: measuring the number of LPDs whose sizes are equal to or greater than the predetermined value in a wafer plane from the wafer surface and an average value and a standard deviation of haze signals in the wafer plane on a wafer-by-wafer basis; sorting out a semiconductor wafer whose number of measured LPDs per wafer is equal to or smaller than a predetermined number from the semiconductor wafers subjected to the measurement; and judging a semiconductor wafer of the semiconductor wafers subjected to the sorting to be a non-defective wafer on condition that a value of Y calculated from the following equation (1) is equal to or smaller than a predetermined value.

$$Y = \sigma/\mu \tag{1}$$

where $\sigma$ is the in-plane standard deviation of the haze signals, and $\mu$ is the in-plane average value of the haze signals.

According to a third aspect of the present invention, a system for judging whether a semiconductor wafer of a plurality of semiconductor wafers is a non-defective wafer based on the number of LPDs measured by setting a minimum size of an LPD to be detected at a predetermined value of 65 nm or less when the number of LPDs on the surfaces of the plurality of semiconductor wafers on which no device pattern is formed is measured for each wafer with a detecting apparatus using a laser scattering method, the system includes: a unit measuring the number of LPDs whose sizes are equal to or greater than the predetermined value in a wafer plane from the wafer surface and an average value and a standard deviation of haze signals in the wafer plane on a wafer-by-wafer basis; a unit sorting out a semiconductor wafer whose number of measured LPDs per wafer is equal to or smaller than a predetermined number from the semiconductor wafers subjected to the measurement; and a unit judging a semiconductor wafer of the semiconductor wafers subjected to the sorting to be a non-defective wafer on condition that a value of Y calculated from the following equation (1) is equal to or smaller than a predetermined value.

$$Y = \sigma/\mu \tag{1}$$

where $\sigma$ is the in-plane standard deviation of the haze signals, and $\mu$ is the in-plane average value of the haze signals.

With the judgment method according to the first aspect of the present invention, a semiconductor wafer whose number of LPDs per wafer is equal to or smaller than a predetermined number is sorted out, and, from the semiconductor wafers obtained by the sorting, a semiconductor wafer is sorted out by checking a haze map generated by the haze signals in a wafer plane by a sensory method conducted by human eyes, and this semiconductor wafer is judged to be a non-defective wafer, whereby it is possible to judge whether a semiconductor wafer is a non-defective wafer or a defective wafer more uniformly without dependence on the difference in the S/N ratio between inspection apparatuses using the laser scattering method. Moreover, it is possible to make up a shipment lot, which is not rejected in the acceptance inspection conducted by the device manufacturer.

With the judgment method according to the second aspect of the present invention, a semiconductor wafer whose number of LPDs per wafer is equal to or smaller than a predetermined number is sorted out, and, from the semiconductor wafers obtained by the sorting, a semiconductor wafer whose average value and standard deviation of the haze signals in a wafer plane have a specific relationship is sorted out, and this semiconductor wafer is judged to be a non-defective wafer, whereby it is possible to judge whether a semiconductor wafer is a non-defective wafer or a defective wafer more uniformly without using a sensory method such as a visual inspection and without dependence on the difference in the S/N ratio between inspection apparatuses using the laser scattering method. Moreover, it is possible to make up a shipment lot, which is not rejected in the acceptance inspection conducted by the device manufacturer.

With the non-defective wafer judgment system according to the third aspect of the present invention, since the system includes a unit measuring the number of LPDs whose sizes are equal to or greater than a predetermined value in a wafer plane from a wafer surface and an average value and a standard deviation of haze signals in the wafer plane on a wafer-by-wafer basis; a unit sorting out a semiconductor wafer whose number of measured LPDs per wafer is equal to or smaller than a predetermined number from the semiconductor wafers subjected to the measurement; and a unit judging a semiconductor wafer of the semiconductor wafers subjected to the sorting to be a non-defective wafer on condition that a value of Y calculated from the following equation (1) is equal to or smaller than a predetermined value, it is possible to judge whether a semiconductor wafer is a non-defective wafer or a defective wafer easily and more uniformly without dependence on the difference in the S/N ratio between inspection apparatuses using the laser scattering method.

$$Y = \sigma/\mu \qquad (1)$$

where σ is the in-plane standard deviation of the haze signals, and μ is the in-plane average value of the haze signals.

DETAILED DESCRIPTION OF THE PREFERRED EMBODIMENTS

Next, embodiments of the present invention will be described based on the drawings.

The present invention is an improved method for judging whether a semiconductor wafer of a plurality of semiconductor wafers is a non-defective wafer based on the number of LPDs measured by setting a minimum size of an LPD to be detected at a predetermined value in advance when the number of LPDs on the surfaces of the plurality of semiconductor wafers on which a device pattern has not yet been formed is measured for each wafer with a detecting apparatus using a laser scattering method. The present invention solves a problem associated with a disparity between the inspection results obtained by a wafer manufacturer and the inspection results obtained by a device manufacturer when, in particular, a minimum size of an LPD serving as a criterion of judgment is extremely small, that is, when the above predetermined value is set at 65 nm or less.

Figure 7:
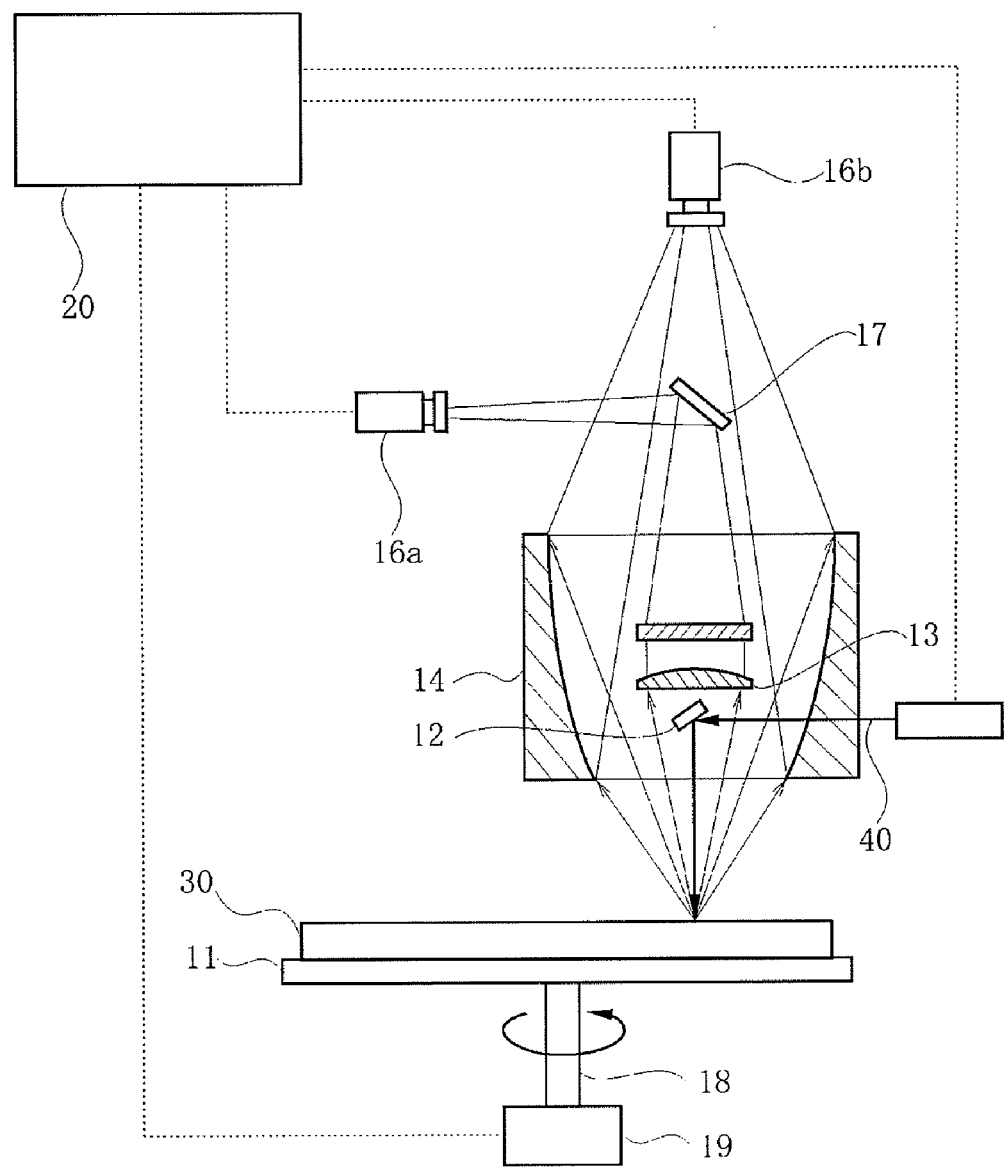
FIG. 7 is a schematic diagram showing the principles of LPD detection in a common inspection apparatus using a laser scattering method.

In a first embodiment of the present invention, first, the number of LPDs whose sizes are equal to or greater than a predetermined value set in advance is measured from the wafer surface, and a haze map on which haze signals in a wafer plane are shown is generated. The predetermined value set in advance is determined by an LPD detection lower limit required by each device manufacturer. This measurement and signal processing are performed by an existing, common inspection apparatus using a laser scattering method. Here, the principles of detection performed by a common inspection apparatus 50 using a laser scattering method will be explained by using FIG. 7.

The inspection apparatus 50 using the laser scattering method uses the fact that the intensity, the angle, etc. of scattered light differ depending on the surface state of a sample. Laser light is made to scan the wafer surface, and the intensity of the scattered light from the wafer surface is measured, whereby an LPD is detected. That is, when the laser light is shone on an area with a particle or surface defect causing an LPD, the intensity of the scattered light in that area is increased as compared to an area with no particle or surface defect. The presence or absence of an LPD is determined by using this fact based on the intensity of the detected scattered light. For example, in FIG. 7, the inspection apparatus 50 includes a rotatable support base 11 for placing a wafer 30 thereon. To the bottom of the support base 11, an upper end of a rotating shaft 18 is connected, and, at a lower end of the rotating shaft 18, a driving unit 19 rotating the support base 11 via the rotating shaft 18 is disposed. Moreover, the inspection apparatus 50 includes a first reflector 12 reflecting laser light 40, a condenser 13 and a light condensing plate 14 which condense the reflected light, a first detector 16a and a second detector 16b, which detect the reflected light, and a second reflector 17 for guiding the reflected light to the first detector 16a. The laser light 40 shone from one direction is reflected downward by the first reflector 12, and is shone onto the surface of the wafer 30 placed on the rotating support base 11. The laser light 40 thus shone is reflected again from the surface of the wafer 30. Part of the reflected light is condensed by the light condensing plate 14, and is detected by the second detector 16b. Moreover, part of the reflected light is condensed by the condenser 13 provided above the first reflector 12, is then reflected by the second reflector 17, and is detected by the first detector 16a. The light scattering which is detected and received by the first detector 16a and the second detector 16b is analyzed by a control unit 20 electrically hard-wired to the first detector 16a, the second detector 16b, and the like, and inspection results such as the number of LPDs are output.

Moreover, as for haze, the inspection apparatus 50 described above detects a haze signal, and this haze signal is analyzed by the control unit 20. Based on the analysis result thus obtained, the average value and the standard deviation of the haze signals are output, and a haze map is generated automatically.

Next, a semiconductor wafer whose number of LPDs per wafer is equal to or smaller than a predetermined number is sorted out from the above-described semiconductor wafers whose numbers of LPDs have been measured. The predetermined number of LPDs which serves as a criterion of sorting is set by negotiations with the device manufacturer as in setting a minimum size of an LPD at a predetermined value as described above. The reason why a semiconductor wafer whose number of measured LPDs is equal to or smaller than a predetermined number is sorted out in advance is as follows. To secure a device yield, it is necessary to manage the cleanliness of the whole production process from production of wafers to production of devices.

Figure 1:
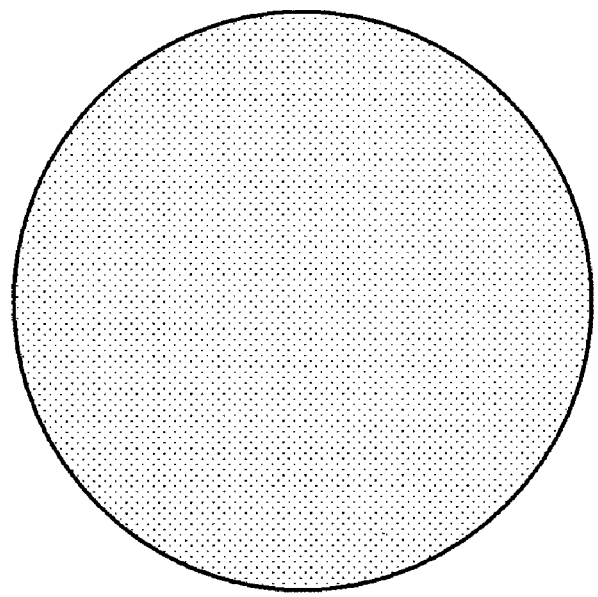
FIG. 1 is a haze map showing a state of the surface of a wafer judged to be a non-defective wafer in Example 1.
Figure 2:
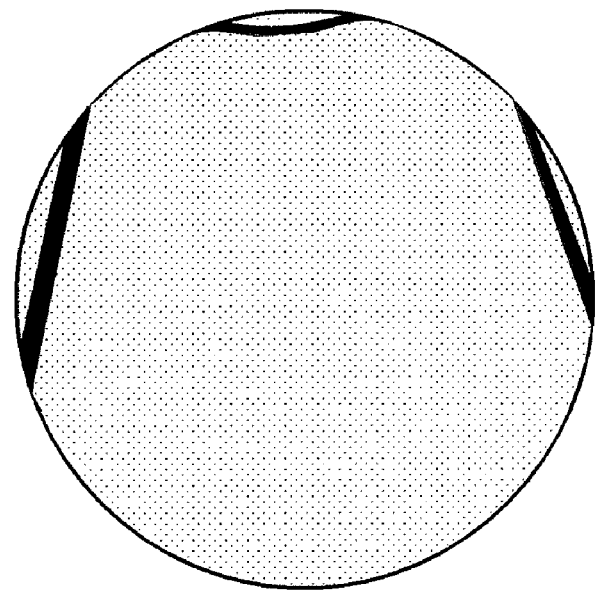
FIG. 2 is a haze map showing a state of the surface of a wafer judged to be a defective wafer in Example 1.

Next, by conducting a visual inspection of a haze map of the semiconductor wafer whose number of LPDs has been measured, a judgment as to whether the wafer is a non-defective wafer or a defective wafer is made. FIG. 1 is a typical schematic view of a haze map of a wafer judged to be a non-defective wafer, and FIG. 2 is a typical schematic view of a haze map of a wafer judged to be a defective wafer. A specific judgment as to whether the wafer is a non-defective wafer or a defective wafer is made as follows. When the haze map exhibits in-plane uniformity as in FIG. 1, the wafer is judged to be a non-defective wafer. On the other hand, when the haze map includes a nonuniform area as in FIG. 2, the wafer is judged to be a defective wafer.

As described above, by a sensory method of making a visual inspection of the haze map, it is possible to judge whether a semiconductor wafer is a non-defective wafer or a defective wafer more uniformly without dependence on the difference in the S/N ratio between inspection apparatuses.

In a second embodiment of the present invention, as is the case with the first embodiment described above, first, the number of LPDs whose sizes are equal to or greater than a predetermined value set in advance is measured from the wafer surface and the in-plane average value and the standard deviation of haze signals in a wafer plane are measured on a wafer-by-wafer basis. As is the case with the first embodiment, the number of LPDs can also be measured by a common inspection apparatus using a laser scattering method.

Next, a semiconductor wafer whose number of LPDs per wafer is equal to or smaller than a predetermined number is sorted out from the above-described semiconductor wafers whose numbers of LPDs have been measured. The predetermined number of LPDs which serves as a criterion of sorting is set by negotiations with the device manufacturer as in setting a minimum size of an LPD at a predetermined value as described above. The reason why a semiconductor wafer whose number of measured LPDs is equal to or smaller than a predetermined number is sorted out in advance is as follows. To secure a device yield, it is necessary to manage the cleanliness of the whole production process from production of wafers to production of devices.

Next, from the semiconductor wafers sorted out as described above, a semiconductor wafer whose value of Y calculated from the following equation (1) is equal to or smaller than a predetermined value is judged to be a non-defective wafer.

$$Y=\sigma/\mu \quad (1)$$

where $\sigma$ is the in-plane standard deviation of the haze signals, and $\mu$ the in-plane average value of the haze signals. The in-plane standard deviation and the in-plane average value are values, which can be measured automatically, and output by the existing inspection apparatus. The value of Y may be calculated manually based on the in-plane standard deviation and the in-plane average value measured automatically by the existing inspection apparatus, or may be calculated automatically by using an inspection apparatus provided with a Y value automatic calculation unit, which will be described later. Moreover, the predetermined value of the value of Y, the predetermined value serving as a criterion of judgment, is set by checking the value against the result of the sensory inspection conducted by humans.

As described above, by using the value of Y calculated based on the haze signals as a criterion of judgment made for a non-defective wafer, it is possible to judge whether a semiconductor wafer is a non-defective wafer or a defective wafer more uniformly and accurately without dependence on the difference in the S/N ratio between inspection apparatuses using the laser scattering method. The technical reason is as follows. In general, in an inspection apparatus using the laser scattering method, since the value of a haze signal automatically measured and output by the inspection apparatus is usually relatively stable in a short period of time such as the time required for an inspection of one wafer when scanning is performed in a wafer plane, the value of a haze signal fluctuates in such a way that an almost constant value is added in the whole plane for each wafer. As a result, instead of using the value of a haze signal output from the inspection apparatus as it is, obtaining a difference or ratio as in equation (1) above makes it possible to reduce the difference in the degree of influence of fluctuations in the sensitivity of each wafer to a minimum and use the obtained value as more accurate data.

Figure 6:
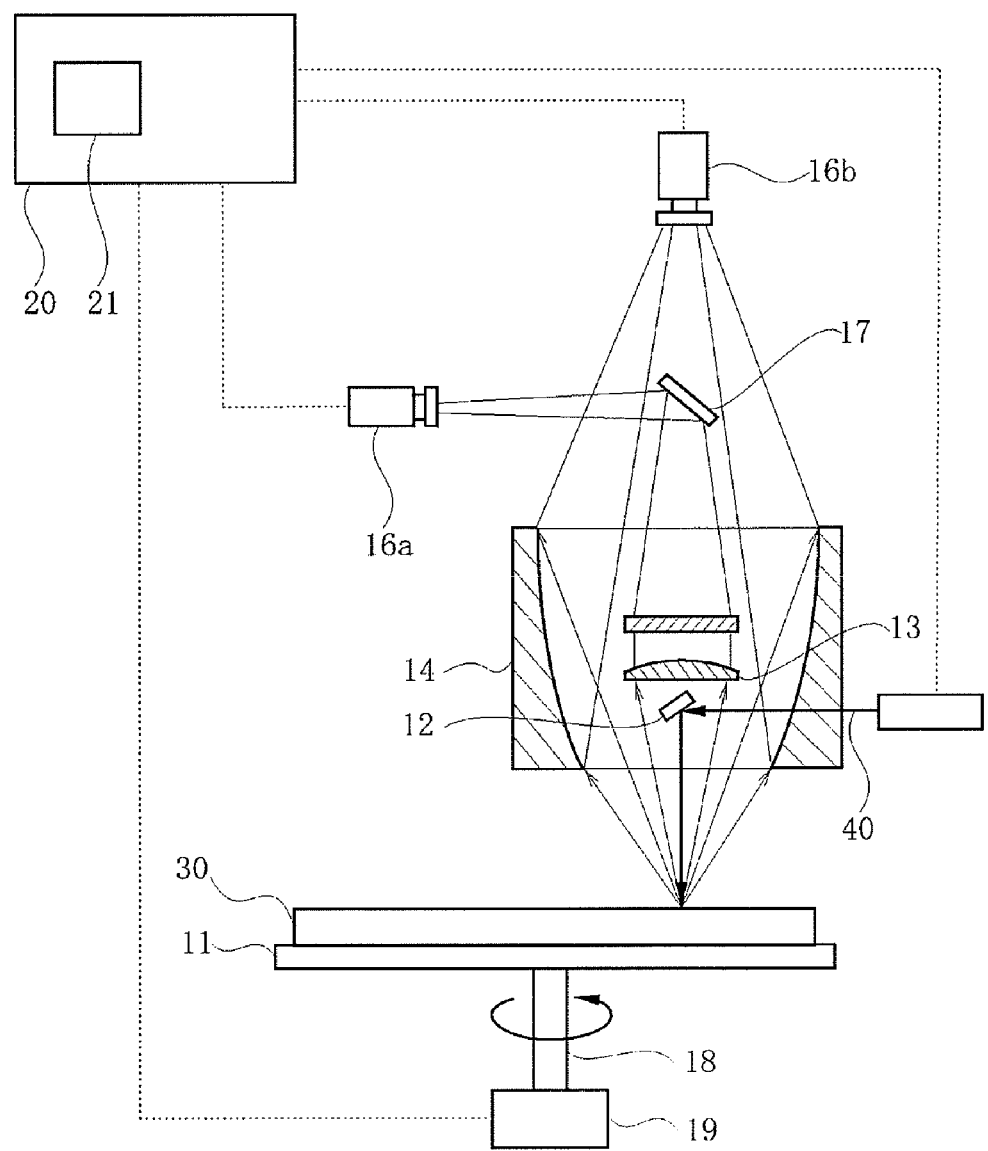
FIG. 6 is a schematic diagram of an inspection apparatus using a laser scattering method, the inspection apparatus used in an embodiment of the present invention.

Next, an inspection apparatus using a laser scattering method, the inspection apparatus used in the method of the present invention for judging whether a semiconductor wafer is a non-defective wafer, will be described. The basic structure of this inspection apparatus is the same as the common inspection apparatus 50 shown in FIG. 7, the inspection apparatus 50 using a laser scattering method. That is, as shown in FIG. 6, this inspection apparatus 10 includes the above-described device for detecting an LPD by making laser light scan the wafer surface and measuring the intensity of the scattered light from the wafer surface. Moreover, a control unit 20 includes an unillustrated unit measuring the number of LPDs on the wafer surface and the in-plane maximum value, the in-plane minimum value, the average value, and the standard deviation of haze signals in a wafer plane on a wafer-by-wafer basis. Furthermore, the control unit 20 further includes a unit 21 calculating the value of Y shown in equation (1) below for each wafer based on the average value and the standard deviation of the haze signals.

$$Y=\sigma/\mu \quad (1)$$

where $\sigma$ is the in-plane standard deviation of the haze signals, and $\mu$ is the in-plane average value of the haze signals. In the past, to carry out the judgment method of the present invention, the value of Y had to be calculated manually from the in-plane average value and standard deviation of the haze signals, the in-plane average value and standard deviation automatically measured by the common inspection apparatus 50 shown in FIG. 7. However, since the inspection apparatus 10 is provided with the control unit 20 including the unit 21 calculating the value of Y, the inspection apparatus 10 can automatically calculate the value of Y for each wafer, making it possible to carry out the judgment method of the present invention more efficiently.

Next, a system of the present invention for judging whether a semiconductor wafer is a non-defective wafer will be described. This non-defective wafer judgment system, has a unit measuring the number of LPDs in a wafer plane from the wafer surface, the LPDs whose sizes are equal to or greater than a predetermined value, and the average value and the standard deviation of haze signals in the wafer plane on a wafer-by-wafer basis. The predetermined value set in advance is determined by an LPD detection lower limit required by each device manufacturer. This measuring unit may be an existing, common inspection apparatus using a laser scattering method, or an apparatus or the like having the same function as the existing, common inspection apparatus using a laser scattering method.

Moreover, the non-defective wafer judgment system has a unit sorting out a semiconductor wafer from the semiconductor wafers subjected to the above measurement, the semiconductor wafer whose number of LPDs per wafer is equal to or smaller than a predetermined number. This sorting unit may be a human unit. Alternatively, this sorting unit may be an apparatus or the like having the function of comparing the number of LPDs thus measured with the predetermined number set in advance, automatically discriminating between a wafer whose number of LPDs is equal to or smaller than the predetermined number and a wafer whose number of LPDs exceeds the predetermined number, and sorting the wafers. The predetermined number of LPDs which serves as a criterion of sorting is set by negotiations with the device manufacturer as in setting a minimum size of an LPD at a predetermined value as described above.

Moreover, the non-defective wafer judgment system has a unit judging a semiconductor wafer whose value of Y calculated from equation (1) below is equal to or smaller than a predetermined value to be a non-defective wafer from the semiconductor wafers obtained by the sorting.

$$Y=\sigma/\mu \quad (1)$$

where $\sigma$ is the in-plane standard deviation of haze signals, and $\mu$ is the in-plane average value of haze signals. The in-plane standard deviation and the in-plane average value are values measured by the measuring unit of the non-defective wafer judgment system of the present invention. The value of Y may be calculated by a human unit performing calculation manually based on the in-plane standard deviation and the in-plane average value obtained by the measurement, or may be calculated by an inspection apparatus or the like including the above-described Y value automatic calculation unit. In addition, the predetermined value of the value of Y, the predetermined value serving as a criterion of judgment, is set by checking the predetermined value against the result of the sensory inspection conducted by humans.

As described above, with the system of the present invention for judging whether a semiconductor wafer is a non-defective wafer, it is possible to judge whether a semiconductor wafer is a non-defective wafer or a defective wafer more uniformly and accurately without dependence on the difference in the S/N ratio between inspection apparatuses using the laser scattering method.

EXAMPLE

Next, examples of the present inventions will be explained together with comparative examples.

Example 1

First, a plurality of semiconductor wafers (diameter: 30 cm) obtained from a silicon single crystal grown by the CZ process (Czochralski process) through a slicing process, a chamfering process, a polishing process, and the like, were prepared. These wafers met the conditions set by negotiations with the device manufacturer, the conditions related to the number of LPDs of 60 nm or more, the LPDs measured by an inspection apparatus (model name: SP1 manufactured by KLA-Tencor Corporation) using a laser scattering method.

Next, a judgment as to whether each of the plurality of wafers meeting the conditions related to the number of LPDs is a non-defective wafer or a defective wafer is made visually based on the haze map obtained by the inspection apparatus. A typical haze map of a wafer judged to be a non-defective wafer is shown in FIG. 1, and a typical haze map of a wafer judged to be a defective wafer is shown in FIG. 2. As for a criterion of judgment visually made for a non-defective wafer and a defective wafer based on the haze map, a wafer is judged to be a non-defective wafer when the haze map exhibits in-plane uniformity as in FIG. 1, and a wafer is judged to be a defective wafer when the haze map includes a nonuniform area as in FIG. 2.

In the shipment inspection conducted by the wafer manufacturer based on the judgment results, one shipment lot was made up of only the wafers judged to be non-defective wafers, and this lot was shipped to the device manufacturer. The yield in the acceptance inspection conducted for this lot by the device manufacturer is shown in table 1 below. Incidentally, in the acceptance inspection conducted by the device manufacturer, a wafer whose number of LPDs of 60 nm or more meets the condition determined by the negotiations is judged to be a non-defective wafer by an inspection apparatus using a laser scattering method.

Example 2

As is the case with Example 1, first, a plurality of semiconductor wafers (diameter: 30 cm) obtained from a silicon single crystal grown by the CZ process (Czochralski process) through a slicing process, a chamfering process, a polishing process, and the like, were prepared. These wafers met the conditions set by negotiations with the device manufacturer, the conditions related to the number of LPDs of 60 nm or more, the LPDs measured by the same inspection apparatus as that used in Example 1.

Next, the in-plane standard deviation σ of the haze signals and the in-plane average value μ of the haze signals were measured with the inspection apparatus using the laser scattering method for each of the plurality of wafers meeting the conditions related to the number of LPDs. Furthermore, based on the measured in-plane standard deviation σ of the haze signals and the measured in-plane average value μ of the haze signals, the value of Y shown in the following equation (1) was obtained.

$$Y = \sigma/\mu \quad (1)$$

Figure 3:
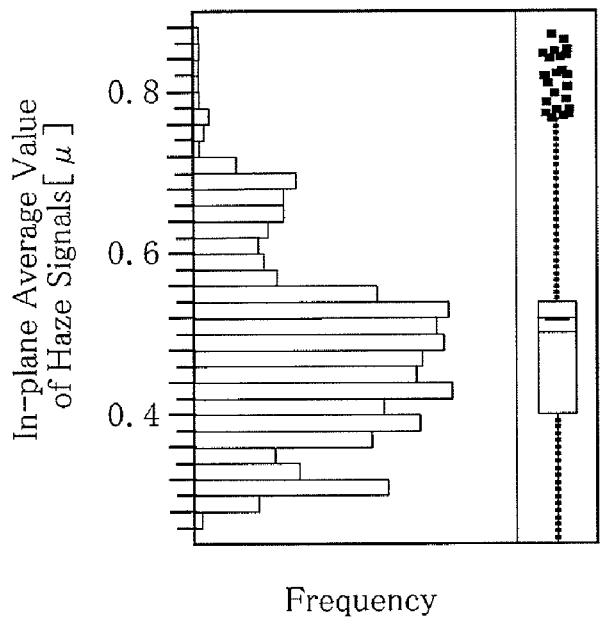
FIG. 3 is a frequency distribution chart showing the number of wafers relative to the in-plane average value of the haze signals measured in Example 2.
Figure 4:
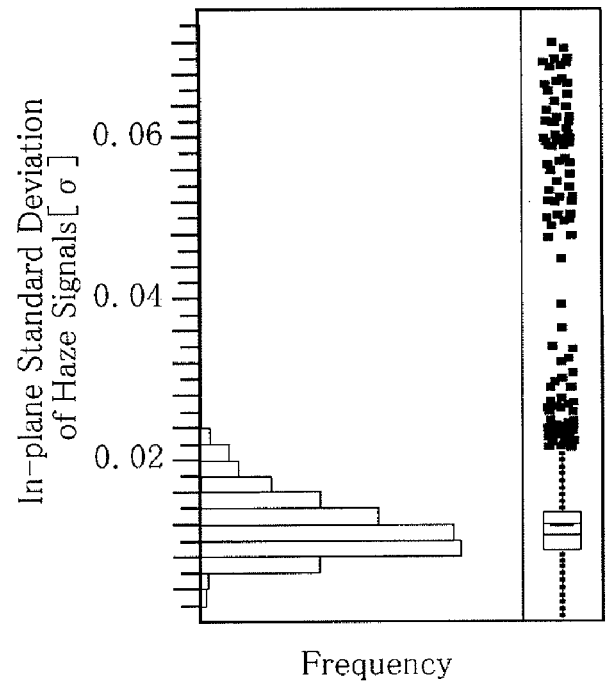
FIG. 4 is a frequency distribution chart showing the number of wafers relative to the in-plane standard deviation of the haze signals measured in Example 2.
Figure 5:
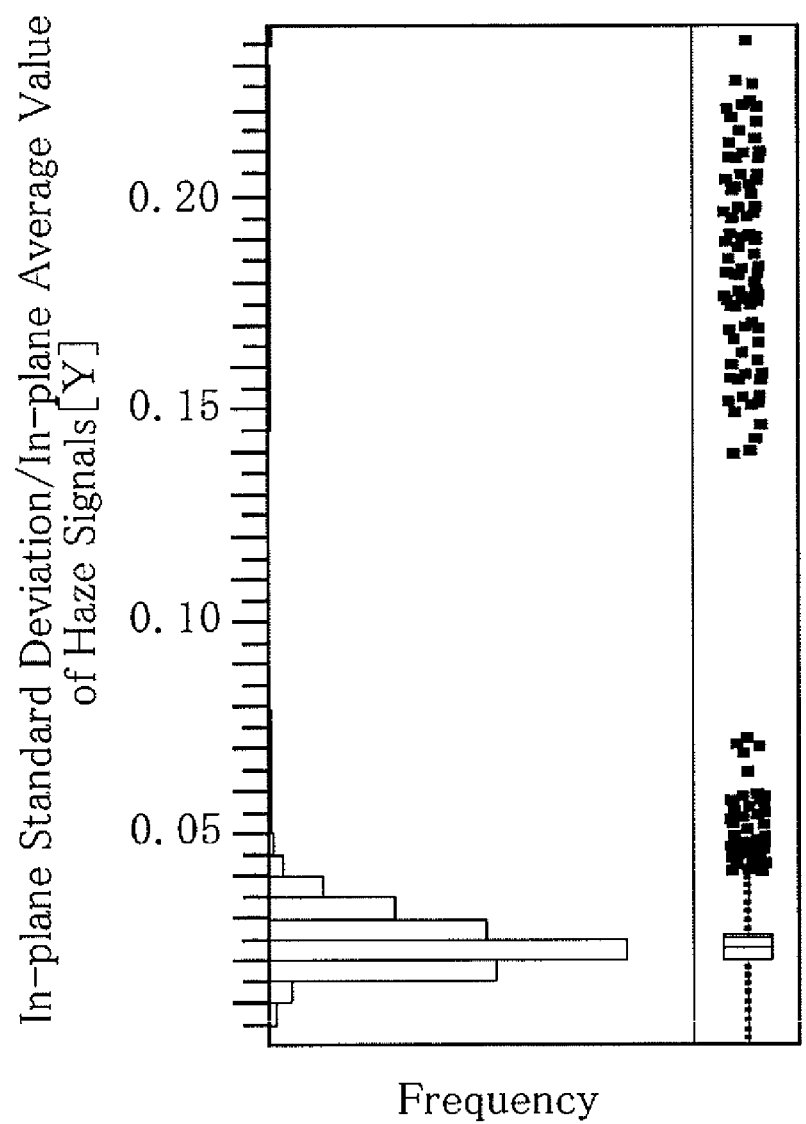
FIG. 5 is a frequency distribution chart showing the number of wafers relative to the values of Y of the haze signals measured in Example 2.

A frequency distribution chart of 100 wafers whose values of Y were calculated one by one in the manner as described above, the frequency distribution chart in which the number of wafers relative to the value of Y is set as a frequency, is shown in FIG. 5. At the same time, a frequency distribution chart of these wafers, the frequency distribution chart in which the number of wafers relative to the in-plane average value μ of the haze signals is set as a frequency, is shown in FIG. 3, and a frequency distribution chart of these wafers, the frequency distribution chart in which the number of wafers relative to the in-plane standard deviation σ of the haze signals is set as a frequency, is shown in FIG. 4. Based on the detection status shown in FIG. 5, a wafer whose value of Y is 0.100 or less was judged to be a non-defective wafer, and a wafer whose value of Y exceeds 0.100 was judged to be a defective wafer. Incidentally, the value of Y of the wafer shown in FIG. 1, the wafer judged to be a non-defective wafer in Example 1, was 0.051, and the value of Y of the wafer shown in FIG. 2, the wafer judged to be a defective wafer, was 0.152.

In the shipment inspection conducted by the wafer manufacturer based on the judgment results, one shipment lot was made up of only the wafers judged to be non-defective wafers, and this lot was shipped to the device manufacturer. The yield in the acceptance inspection conducted for this lot by the device manufacturer is shown in table 1 below. Incidentally, in the acceptance inspection conducted by the device manufacturer, a wafer whose number of LPDs of 60 nm or more meets the condition determined by the negotiations is judged to be a non-defective wafer by an inspection apparatus using a laser scattering method.

Comparative Example 1

As is the case with Example 1, first, a plurality of semiconductor wafers (diameter: 30 cm) obtained from a silicon single crystal grown by the CZ process (Czochralski process) through a slicing process, a chamfering process, a polishing process, and the like, were prepared. These wafers met the conditions set by negotiations with the device manufacturer, the conditions related to the number of LPDs of 60 nm or more, the LPDs measured by the same inspection apparatus as that used in Example 1.

In the shipment inspection conducted by the wafer manufacturer based only on the judgment results, one shipment lot was made up of only the wafers judged to be non-defective wafers, and this lot was shipped to the device manufacturer. The yield in the acceptance inspection conducted for this lot by the device manufacturer is shown in table 1 below. Incidentally, in the acceptance inspection conducted by the device manufacturer, a wafer whose number of LPDs of 60 nm or more meets the condition determined by the negotiations is judged to be a non-defective wafer by an inspection apparatus using a laser scattering method.

Comparative Example 2

As is the case with Example 1, first, a plurality of semiconductor wafers (diameter: 30 cm) obtained from a silicon single crystal grown by the CZ process (Czochralski process) through a slicing process, a chamfering process, a polishing process, and the like, were prepared. These wafers met the conditions set by negotiations with the device manufacturer, the conditions related to the number of LPDs of 80 nm or more, the LPDs measured by the same inspection apparatus as that used in Example 1.

In the shipment inspection conducted by the wafer manufacturer based only on the judgment results, one shipment lot was made up of only the wafers judged to be non-defective wafers, and this lot was shipped to the device manufacturer. The yield in the acceptance inspection conducted for this lot by the device manufacturer is shown in table 1 below. Incidentally, in the acceptance inspection conducted by the device manufacturer, a wafer whose number of LPDs of 80 nm or more meets the condition determined by the negotiations is judged to be a non-defective wafer by an inspection apparatus using a laser scattering method.

TABLE 1

| | | Yield (%) | |
|---|---|---|---|
| | Minimum size of an LPD to be detected [nm] | Inspection by wafer manufacturer (shipment inspection) | Inspection by device manufacturer (acceptance inspection) |
| Example 1 | 60 | 100 | 100 |
| Example 2 | 60 | 100 | 100 |
| Comparative Example 1 | 60 | 100 | 92 |
| Comparative Example 2 | 80 | 100 | 100 |

As is clearly shown in table 1, a comparison between Examples 1 and 2 and Comparative Example 1 revealed that, in Comparative Example 1 in which a judgment was made based only on the number of LPDs, there was a wafer whose judgment results differed in the shipment inspection conducted by the wafer manufacturer and the acceptance inspection conducted by the device manufacturer. On the other hand, in Examples 1 and 2, the results of the shipment inspection conducted by the wafer manufacturer coincided with the results of the acceptance inspection conducted by the device manufacturer. These results confirm that the judgment method of the present invention is more accurate. Moreover, based on comparisons between FIGS. 3 to 5, the following facts can be confirmed. In FIGS. 3 and 4, the frequency distribution is sparse and there is no outstanding peak, making it difficult to set a criterion of judgment made for a non-defective wafer and a defective wafer from FIGS. 3 and 4; on the other hand, in FIG. 5, that is, in the frequency distribution chart in which the values of Y are calculated, the frequency distribution includes an outstanding peak, making it easy to set a criterion of judgment made for a non-defective wafer and a defective wafer. In addition, as in Comparative Example 2 in which a minimum size of an LPD serving as a criterion of judgment is relatively large, such as a size of more than 65 nm, no disparity is created between the judgment results obtained by the wafer manufacturer and the judgment results obtained by the device manufacturer without applying the present invention.

What is claimed is:

1. A method for judging whether a semiconductor wafer is a non-defective wafer by using a laser scattering method, the method for judging whether a semiconductor wafer of a plurality of semiconductor wafers is a non-defective wafer based on the number of LPDs measured by setting a minimum size of an LPD to be detected at a predetermined value of 65 nm or less when the number of LPDs on the surfaces of the plurality of semiconductor wafers on which no device pattern is formed is measured for each wafer with a detecting apparatus using a laser scattering method, the method comprising a step of:

measuring the number of LPDs whose sizes are equal to or greater than the predetermined value in a wafer plane from the wafer surface and an average value and a standard deviation of haze signals in the wafer plane on a wafer-by-wafer basis;

sorting out a semiconductor wafer whose number of measured LPDs per wafer is equal to or smaller than a predetermined number from the semiconductor wafers subjected to the measurement; and judging a semiconductor wafer of the semiconductor wafers subjected to the sorting to be a non-defective wafer on condition that a value of Y calculated from the following equation (1) is equal to or smaller than a predetermined value;

$$Y = \sigma/\mu \tag{1}$$

where $\sigma$ is the in-plane standard deviation of the haze signals, and $\mu$ is the in-plane average value of the haze signals.

2. A system for judging whether a semiconductor wafer is a non-defective wafer by using a laser scattering method, the system for judging whether a semiconductor wafer of a plurality of semiconductor wafers is a non-defective wafer based on the number of LPDs measured by setting a minimum size of an LPD to be detected at a predetermined value of 65 nm or less when the number of LPDs on the surfaces of the plurality of semiconductor wafers on which no device pattern is formed is measured for each wafer with a detecting apparatus using a laser scattering method, the system comprising:

a unit measuring the number of LPDs whose sizes are equal to or greater than the predetermined value in a wafer plane from the wafer surface and an average value and a standard deviation of haze signals in the wafer plane on a wafer-by-wafer basis;

a unit sorting out a semiconductor wafer whose number of measured LPDs per wafer is equal to or smaller than a predetermined number from the semiconductor wafers subjected to the measurement; and a unit judging a semiconductor wafer of the semiconductor wafers subjected to the sorting to be a non-defective wafer on condition that a value of Y calculated from the following equation (1) is equal to or smaller than a predetermined value;

$$Y = \sigma/\mu \tag{1}$$

where $\sigma$ is the in-plane standard deviation of the haze signals, and $\mu$ is the in-plane average value of the haze signals.

* * * * *